United States Patent [19]
Cole

[11] Patent Number: 5,931,014
[45] Date of Patent: Aug. 3, 1999

[54] DUCTWORK PURIFICATION SYSTEM

[75] Inventor: William Lesley Cole, Aldershot, United Kingdom

[73] Assignee: Ozone Industries Limited, Farnborough, United Kingdom

[21] Appl. No.: 09/040,753

[22] Filed: Mar. 18, 1998

[30]     Foreign Application Priority Data

May 15, 1997 [GB]  United Kingdom ................... 9709876

[51] Int. Cl.[6] .............................. F25D 23/12; B01J 19/12
[52] U.S. Cl. ........................................ 62/264; 422/186.07
[58] Field of Search ........................ 422/186.07, 186.15; 134/43; 62/264

[56]                 References Cited

U.S. PATENT DOCUMENTS

| 724,554 | 4/1903 | Davis . | |
|---|---|---|---|
| 2,212,109 | 8/1940 | Abraham | 62/89 |
| 2,248,713 | 7/1941 | Locke | 21/74 |
| 3,750,556 | 8/1973 | Duke | 98/2.11 |
| 4,552,659 | 11/1985 | Tabata et al. . | |
| 5,705,131 | 1/1998 | Rutland | 422/186.07 |

FOREIGN PATENT DOCUMENTS

| A2 0 390 159 | 10/1990 | European Pat. Off. . |
| A 2 273 048 | 6/1994 | United Kingdom . |
| A 2 301 175 | 11/1996 | United Kingdom . |

*Primary Examiner*—Henry A. Bennett
*Assistant Examiner*—Melvin Jones
*Attorney, Agent, or Firm*—Oliff & Berridge, PLC

[57]                 ABSTRACT

The invention relates to a ductwork and cleaning system comprising a fogging unit to supply atomised water droplets to the interior of a food storage cabinet with an ozone generating means coupled to the ductwork, such that ozone, generated by the ozone generating means, is supplied to the interior of the ductwork for circulating therethrough, thereby cleaning the ductwork. The food storage cabinet is coupled to a refrigeration unit to provide refrigerated air for the food storage cabinet, some of the refrigerated air being used as the oxygen-containing gas for the ozone generating means. The ozone generating means is pererably arranged in series in the flow path of the fog of atomised water droplets.

6 Claims, 3 Drawing Sheets

DUCTWORK PURIFICATION SYSTEM

FIELD OF THE INVENTION

This invention relates to a system for cleansing ductwork, particularly, although not exclusively, for use with food refrigeration cabinets.

BACKGROUND OF THE INVENTION

In retail outlets, for example, in supermarkets, where fresh food is displayed to the consumer it is necessary to keep the food fresh. Often, food, for example, cold meats and other delicatessen foods, are displayed in a refrigerated cabinet. However, food that is kept in such a way has a tendency to dry out over time as it loses air to the atmosphere—particularly, where the environment is a refrigerated environment. In order to counteract these drying effects, moisture is added to the atmosphere in the cabinet. This is achieved by producing a fog of finely atomised water droplets which has the effect of neutralising the moisture loss from the food.

This fog of atomised water droplets is delivered into the refrigeration cabinets through plastic piping or ductwork. However, some water remains in the ductwork and becomes a potential breeding ground for bacteria, which can then be delivered by the fog to the food on display or into the cabinet itself. Naturally, this means that there is a potentially extremely dangerous source of bacterial infection. It is extremely important, therefore, that the ductwork should be regular cleaned in order to remove bacteria, and other potential sources of infection such as mould, fungus or yeast.

Cleaning the ductwork can be difficult, if not impossible, as it is not always possible to reach all parts of the system with conventional known cleaning techniques.

SUMMARY OF THE INVENTION

According to the present invention, there is provided a pipework cleaning system comprising an ozone generating means coupled to the pipework, such that ozone generated by the ozone generating means is supplied to the interior of the pipework for circulating therethrough, thereby cleaning the pipework. The pipework may be that of a fogging unit for a food storage cabinet from which an oxygen-containing gas for use by the ozone generating unit to generate ozone therefrom is supplied. The oxygen-containing gas may be air, coupled to the ozone generating unit via a refrigeration unit used to supply refrigerated air to the food storage cabinet.

BRIEF DESCRIPTION OF THE DRAWINGS

The invention will now be described, by way of example only, with reference to the accompanying drawings, of which.

DETAILED DESCRIPTION OF THE EMBODIMENTS

Figure 1:
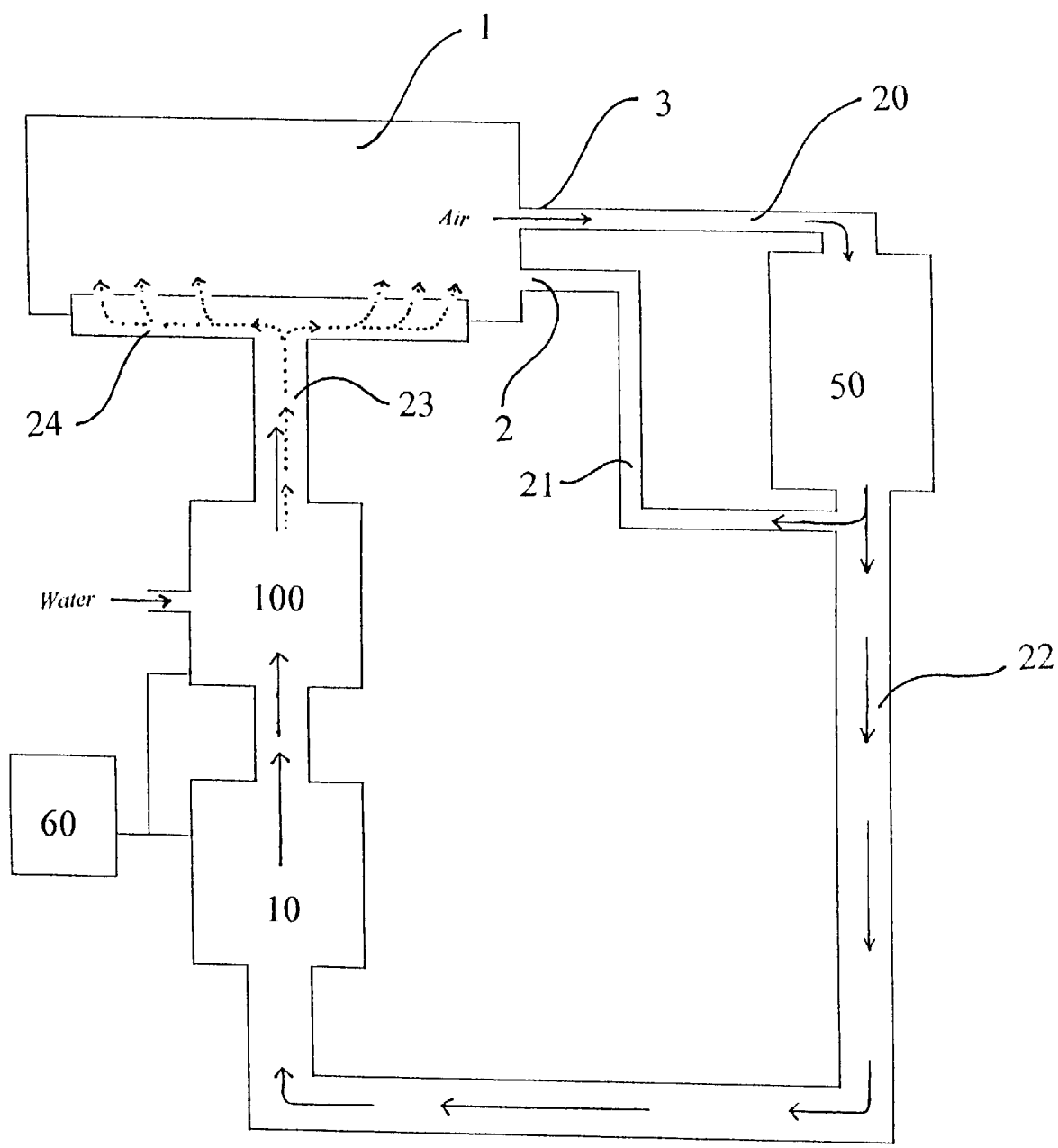
FIG. 1 is a block diagram illustrating a system for purifying the ductwork of a refrigeration cabinet fogging unit, showing the flow of air, and generated fog, through the system.
Figure 2:
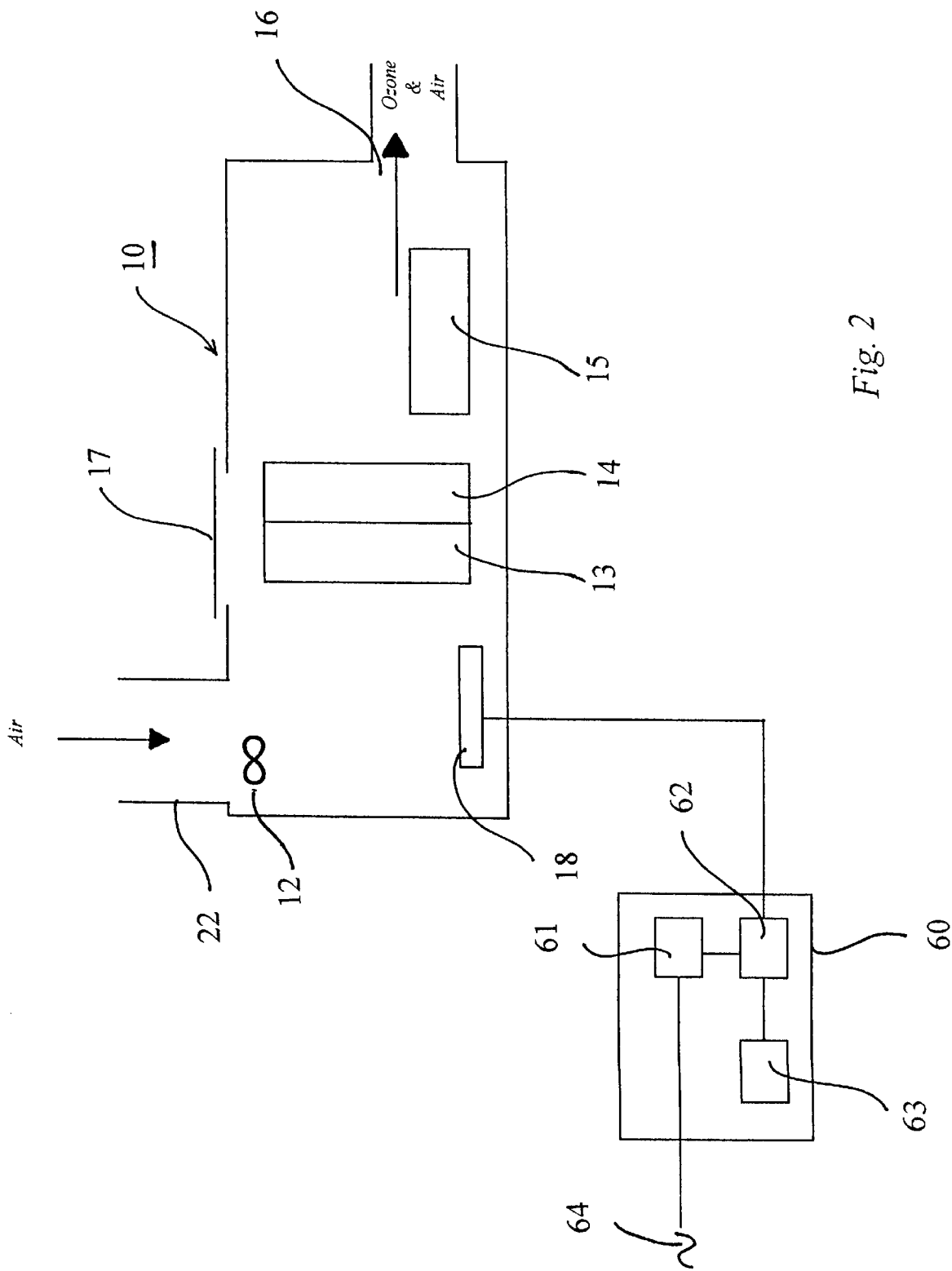
FIG. 2 is a schematic of an ozone generating unit and control unit of the system of FIG. 1.
Figure 3:
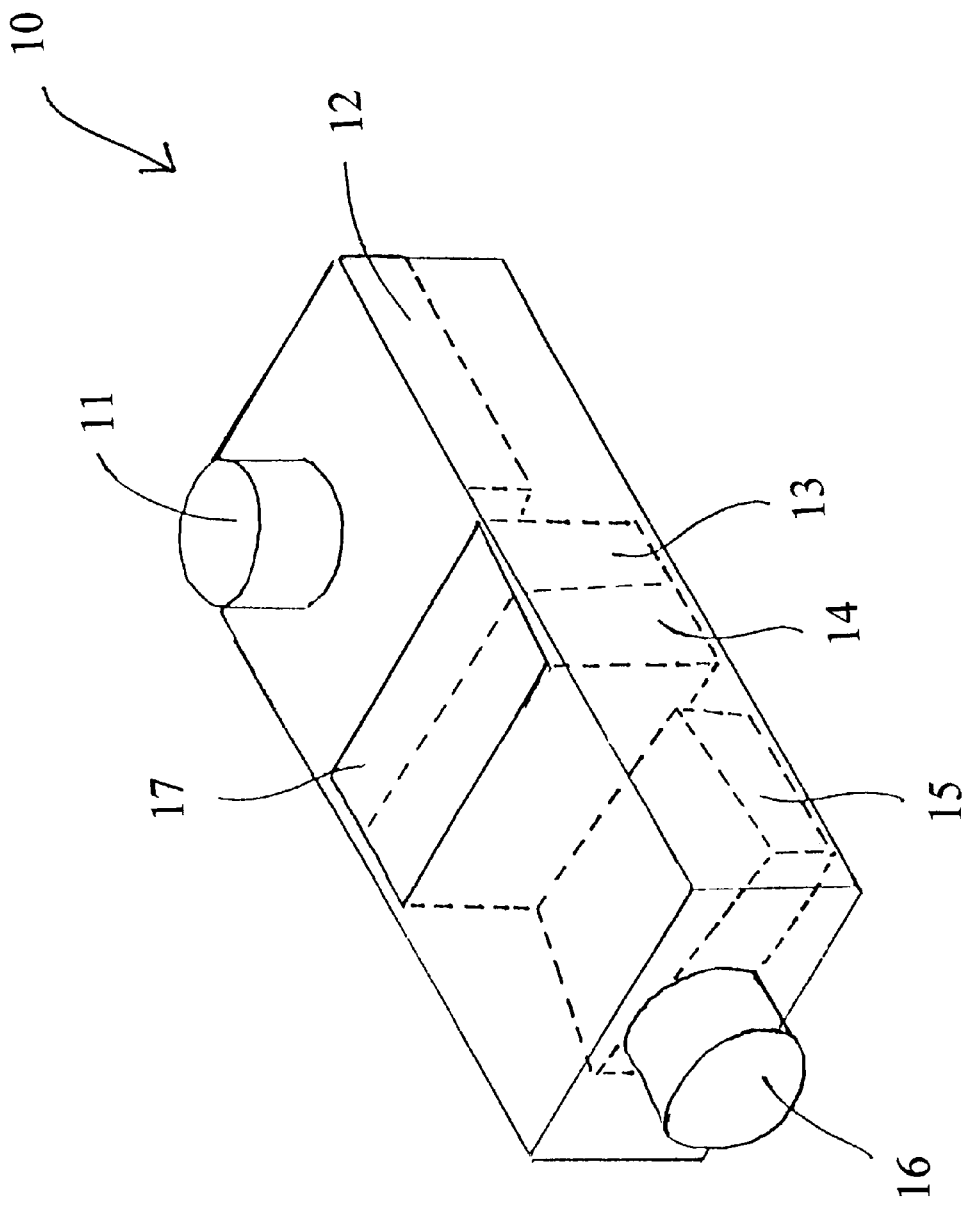
FIG. 3 is a perspective view of the ozone generating unit.

A refrigeration cabinet 1 is used to display a variety of fresh foods, for example, delicatessen foods. To refrigerate the contents of the cabinet 1, air is fed from the cabinet 1 via an air outlet 3 and ductwork 20 to a refrigeration unit 50—conventionally sited underneath the refrigeration cabinet 1. Refrigerated air is then fed back to the cabinet 1 from the refrigeration unit 50, via ductwork 21 and refrigerated air inlet 2. This process of recirculating the air via the refrigeration unit 50 provides a constantly refrigerated environment within the cabinet which helps to maintain the freshness of the contents of the cabinet. The refrigeration unit 50 is of a known type, and, as such need not be discussed in any further details herein. The cabinet 1 can be substantially enclosed, or may be open to allow easy access to the contents.

As discussed in the preamble, it is known to provide a fog of atomised water droplets in the refrigeration cabinet 1 to counteract the drying effects of the refrigeration, and the fact that the contents of the cabinet are left exposed to the air. A fogging unit 100 is used to generate fog using water supplied through water inlet 101. The fog is then supplied to the cabinet 1 via ductwork 23,24. This flow of fog is illustrated by the dotted arrows in FIG. 1. Air flow, and, where applicable, ozone flow, is indicated by bold arrows. The provision of a fogging unit 100, and the method of supplying the fog to a refrigeration cabinet 1 is, in itself, well known to persons skilled in the art, and need not be described in any further detail herein, except as is relevant to the present invention.

Some of the air from the refrigeration unit 50 is fed via ductwork 22 to an ozone generation unit 10. Air is fed into the ozone generation unit 10 through an air inlet 11 of the ozone generation unit 10 where a fan 12 moves the stream of air through the ozone generation unit 10, where it passes through, initially, through a first and second filter 13,14, and then over an ozone generating cell 15, which generates ozone from the air passing in its vicinity. The ozone generating cell 15 comprises electrodes (not shown) provided on ceramic plates (not shown) which generate ozone in the region of the electrodes when a high-tension voltage supply is coupled to the electrodes. This method of generating ozone is already known, and as such, need not be described in any more detail herein.

In this embodiment the ozone generation unit 10 is in series with the ductwork and arranged in line and in the flow of the duct work. In an alterantive embodiment the ozone generating unit 10 may be arrranged to be parallel with the ductwork in an off-line position out of the normal flow of the fog, and the oxone may then join the ductwork from one side when it is activated to carry out the disinfecting function when required.

The fan 12 is a variable speed DC fan, and the filters 13,14 will be made of an ozone resistant material as is known to persons skilled in the art. The filter are used to remove any particulate matter from the air. Typically, the ozone generation unit 10 will be made from stainless steel. The filters 13,14 are accessible through a hatch 17 to allow replacement.

The generated ozone may be then fed out of the ozone generating unit 10 through an ozone outlet 16, via the fogging unit 100 into the ductwork 23,24 which is used to supply the generated fog of atomised water droplets to the refrigeration cabinet as discussed above.

While the refrigeration cabinet 1 is being used to display food, for example, during shop hours, then the ozone generation unit 10 is not in operation, and the refrigeration unit 50 is used to provide refrigerated air to the cabinet 1, and, at the same time, the fogging unit 101 is used to provided a fog to help neutralise the drying effects of refrigeration. The process is continued throughout normal operation of the cabinet, i.e. when it is being used to display food, for example, during trading hours.

At some period during the time outside normal operating hours, for example at night, the fogging unit 100 is switched off, and the ozone generation unit 10 is switched on. Refrigeration may still be taking place, but this is not essential.

During this mode of operation, when the fogging unit 100 is switched off, the ozone generation unit 10 is switched on, and air—which may or may not be refrigerated during the process—is fed from the cabinet 1, via air outlet 3, ductwork 20, refrigeration unit 50, and ductwork 22 to the ozone generation unit 10 where it is used to generate ozone—as described above. The generated ozone is then fed via outlet 16 to the ductwork 23,24 and circulated through it. Now, ozone is a known bactericide which is capable of killing bacteria and other harmful substances as well as being able to neutralise unpleasant odours and noxious substances. It is unstable and soon breaks down to oxygen thereby leaving no harmful residues or odours. By circulating the ozone through the ductwork 23,24, bacteria and other harmful substances lying in the ductwork 23,24 are destroyed, and the ductwork 23,24 cleansed. Once the ductwork 23,24 has been cleaned, then the fogging unit 100 may be switched on as required. Typically, the ozone generation unit 10 will be operable to provide an ozone concentration of between 1 and 2 parts per million, and is switched on for approximately two hours within a twenty four hour period.

The operation of the ozone generation unit 10 and the fogging unit 100 is controlled by a control unit 60. The control unit 60 is coupled to a mains supply 64 and includes a mains transformer 61, a control printed circuit board 62, timer 63 and is coupled to a terminal box 18 provide within the ozone generation unit 10. The operation of the fan 12 is also controlled by the control unit 60.

As will be understood by persons skilled in the art, various modifications are possible within the scope of the present invention. For example, any known suitable ozone generation method can be used. The present invention can be applied to any system using ductwork which is susceptible to contamination. The mode of operation can also include the production of ozone at the same time as the fogging procedure is being carried out. This may have the added advantage of sterilising the water used in the production of the fog, however, this may also have the disadvantage that the undissolved amount of ozone in the ductwork is reduced thereby leaving insufficient undissolved ozone to carry out the cleaning of the ductwork.

I claim:

1. A ductwork and cleaning system, including a food storage cabinet, said ductwork comprising a fogging unit, the fogging unit being used to supply atomised water droplets to the interior of the food storage cabinet for maintaining the freshness of food stored therein, characterised in that the ozone generating means is coupled to the ductwork, such that the system is operable between a first stage in which the ozone generating means is turned off and the fogging unit is turned on and supplies atomised water droplets to the food storage cabinet, and a second state in which the ozone, generated by the ozone generating means from an oxygen-containing gas, is supplied to the interior of the ductwork and circulated therethrough, thereby cleaning the ductwork and the fogging unit is turned off.

2. A ductwork cleaning system according to claim 1, wherein the oxygen-containing gas for use by the ozone generating means is supplied from the food storage cabinet.

3. A ductwork cleaning system according to claim 2, wherein the food storage cabinet is coupled to a refrigeration unit to provide refrigerated air for the food storage cabinet, some of the refrigerated air being used as the oxygen-containing gas for the ozone generating means.

4. A ductwork cleaning system according to claim 1, wherein the ozone generating means is operable to produce ozone at a time when the fogging unit is not operating to produce a fog of atomised water droplets.

5. A ductwork cleaning system according to claim 1, wherein the ozone generating means and the fogging unit operate simultaneously.

6. A ductwork cleaning system according to claim 1, wherein the ozone generating means is arranged in the ductwork in the normal flow path of the fog.

* * * * *